United States Patent
Panitz et al.

(10) Patent No.: US 11,559,189 B2
(45) Date of Patent: Jan. 24, 2023

(54) STERILE SHEATH FOR CONFOCAL ENDOMICROSCOPY SCANNER PROBE

(71) Applicants: Carl Zeiss Meditec AG, Jena (DE); OPTISCAN Pty Ltd., Mulgrave (AU)

(72) Inventors: Gerald Panitz, Bopfingen (DE); Robert Pattie, Nyora (AU); Peter Maxwell Delaney, Carnegie (AU); Christopher Byrne, Berwick (AU); Selene Rodd-Routley, Berlin (DE)

(73) Assignees: Carl Zeiss Meditec AG, Jena (DE); Optiscan PTY Ltd., Mulgrave (AU)

( * ) Notice: Subject to any disclaimer, the term of this patent is extended or adjusted under 35 U.S.C. 154(b) by 605 days.

(21) Appl. No.: 16/176,471

(22) Filed: Oct. 31, 2018

(65) Prior Publication Data
US 2020/0129049 A1 Apr. 30, 2020

(51) Int. Cl.
*A61B 1/00* (2006.01)
*A61B 90/20* (2016.01)

(52) U.S. Cl.
CPC ........ *A61B 1/00142* (2013.01); *A61B 1/0014* (2013.01); *A61B 1/00089* (2013.01); *A61B 1/00096* (2013.01); *A61B 90/20* (2016.02)

(58) Field of Classification Search
CPC . A61B 1/0142; A61B 1/0014; A61B 1/00135; A61B 5/0068; A61B 90/20; A61B 1/00089; A61B 1/00096
See application file for complete search history.

(56) References Cited

U.S. PATENT DOCUMENTS

| | | | | |
|---|---|---|---|---|
| 4,522,196 A | * | 6/1985 | Cunningham | A61B 1/00142 359/511 |
| 4,683,874 A | * | 8/1987 | Acquista | A61B 1/0008 600/104 |
| 4,974,580 A | * | 12/1990 | Anapliotis | A61B 1/00142 600/122 |
| 5,201,908 A | * | 4/1993 | Jones | A61B 1/00091 600/123 |
| 5,413,092 A | * | 5/1995 | Williams, III | A61B 1/00142 600/125 |
| 5,433,221 A | | 7/1995 | Adair | |

(Continued)

FOREIGN PATENT DOCUMENTS

DE 102006045032 B3 5/2008
EP 1213988 B1 11/2009

*Primary Examiner* — Matthew J Kasztejna
(74) *Attorney, Agent, or Firm* — Falk Ewers; Ewers IP Law PLLC

(57) ABSTRACT

A sterile sheath and methods for enclosing a confocal endomicroscopy (CEM) scanner probe with the sterile sheath are provided. The scanner probe includes a probe shaft, a probe tip, a probe body, and a probe umbilical. The sterile sheath for enclosing the CEM scanner probe includes a sheath tube configured to receive the probe shaft and has a distal tube end, a proximal tube end, a sheath tip mounted at the distal tube end of the sheath tube, and a sheath socket configured to receive the probe body. The sheath socket has a distal socket end and a proximal socket end. The proximal tube end of the sheath tube is fixed to the sheath socket at the distal socket end. The sterile sheath further includes a sheath lock ring and a sheath drape mounted on the sheath socket at the proximal socket end with the sheath lock ring.

15 Claims, 16 Drawing Sheets

(56) References Cited

U.S. PATENT DOCUMENTS

| | | | | |
|---|---|---|---|---|
| 5,536,244 | A * | 7/1996 | Muller | A61B 1/00096 228/124.1 |
| 5,545,121 | A * | 8/1996 | Yabe | A61B 1/00142 206/363 |
| 5,636,625 | A * | 6/1997 | Miyagi | A61M 16/0488 128/200.26 |
| 5,738,630 | A * | 4/1998 | Suzuki | A61B 1/00057 600/121 |
| 5,916,145 | A * | 6/1999 | Chu | A61B 1/00071 600/121 |
| 5,941,815 | A * | 8/1999 | Chang | A61B 1/31 600/114 |
| 6,110,103 | A * | 8/2000 | Donofrio | A61B 1/126 600/114 |
| 6,530,881 | B1 * | 3/2003 | Ailinger | A61B 1/00142 600/114 |
| 6,863,651 | B2 | 3/2005 | Remijan et al. | |
| 6,911,005 | B2 * | 6/2005 | Ouchi | A61B 1/00142 600/121 |
| 7,942,814 | B2 | 5/2011 | Remijan et al. | |
| 8,814,781 | B2 * | 8/2014 | Avitsian | A61B 1/00142 600/121 |
| 10,595,710 | B2 * | 3/2020 | Gill | A61B 1/00167 |
| 2002/0133058 | A1 * | 9/2002 | Calderwood | A61B 1/00142 600/122 |
| 2012/0157771 | A1 * | 6/2012 | Avitsian | A61B 1/00078 600/125 |

* cited by examiner

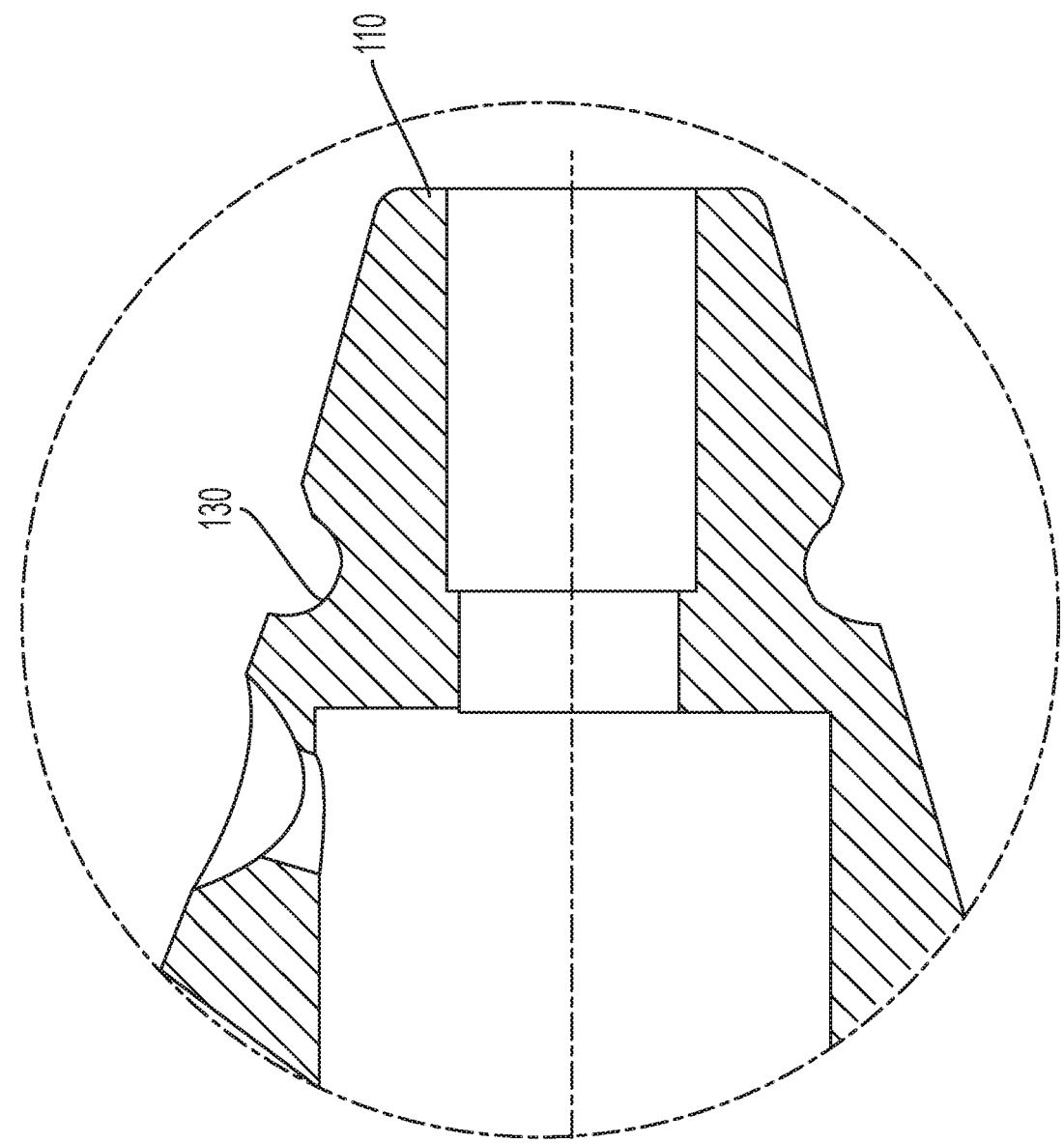

STERILE SHEATH FOR CONFOCAL ENDOMICROSCOPY SCANNER PROBE

TECHNICAL FIELD

The invention relates to a sterile sheath and methods for enclosing non-sterile optical surgical instruments, and in particular to a sterile sheath and methods for enclosing a confocal endomicroscopy (CEM) scanner probe.

BACKGROUND

Optical surgical instruments with direct contact to open wounds in patients are utilized in sterile environments and are handled by sterile medical professionals. In particular endoscopes intended to be inserted into the human body through or into surgically created openings need to be free from biological contaminants. Most optical surgical instruments, however, are too delicate to be sterilized. Therefore, many surgical instruments are covered by drapes or sheaths, some of which have specific sections designed to allow signals to pass through.

Existing drapes for surgical microscopes include a drape part, e.g., a plastic foil, covering loosely the microscope's arm and head, and a window part is provided that has optical properties to allow to send illumination light to the surgical field and to see the situs without aberrations, intensity changes, or color changes.

A windowed self-centering drape for attaching a sterile endoscope to a non-sterile surgical camera is described, for example, in U.S. Pat. No. 5,433,221. The self-centering drape is made of a substantially non-elastic body portion. A paper strip is used to attach the proximal end of the drape to an object such as a camera cable or a viewing monitor. The camera is inserted together with a camera coupler within the drape. A window in the drape is pressed inside a recess of the camera coupler by the sterile endoscope from outside the drape thereby placing the window in alignment along the optical path.

While existing drapes and sheaths provide sterile barriers, these drapes and sheaths do not allow a precise placement of the drape window, which hinders, reduces, or falsifies the signals passing through the drape window. In particular, these existing drapes or sheaths are not applicable to CEM scanner probes with very thin scanner shafts that are employed in the field of cellular imaging, e.g., by neurosurgeons performing a digital biopsy without the need for tissue extraction.

CEM scanners could generally be designed to be robust, e.g., the CEM scanners could be "hardened" so that they could be sterilized using a plasma or a gas. In addition, existing sheaths could be provided with steel pipes and glass windows or other materials that can be reprocessed. However, approaches such as hardening CEM scanners to be sterilized or sheath that can be reprocessed pose significant design challenges, including high development costs, and they also create reliability issues.

In addition, installing existing drapes and sheaths is time consuming and imprecise which negatively impacts the quality of optical signals passing through the drapes and sheaths. Therefore, a fastening arrangement that allows to precisely and securely affix a sterile sheath on an optical surgical instrument in a time-efficient manner prior to imaging is highly desirable.

SUMMARY

It is therefore an object of the present invention to provide a sterile sheath that is easy to be applied prior to imaging and easy to be removed thereafter, that is robust, and that minimizes any adverse effects on signals passing through a window of the sterile sheath.

The object is achieved by providing a sterile sheath for enclosing a CEM scanner probe and methods for securely affixing the sterile sheath to the CEM scanner probe as disclosed herein.

Hereinafter the terms "exhibit", "have", "comprise" or "include" or any grammatical deviations therefrom are used in a non-exclusive way. Accordingly, these terms can refer either to situations in which, besides the feature introduced by these terms, no further features are present, or to situations in which one or more further features are present. For example, the expression "A exhibits B", "A has B", "A comprises B" or "A includes B" may refer both to the situation in which no further element aside from B is provided in A (that is to say to a situation in which A is composed exclusively of B) and to the situation in which, in addition to B, one or more further elements are provided in A, for example element C, elements C and D, or even further elements.

In addition, the terms "at least one" and "one or more" and grammatical modifications of these terms or similar terms, if they are used in association with one or more elements or features and are intended to express the fact that the element or feature can be provided singly or multiply, in general are used only once, for example when the feature or element is introduced for the first time. When the feature or element is subsequently mentioned again, the corresponding term "at least one" or "one or more" is generally no longer used, without restriction of the possibility that the feature or element can be provided singly or multiply.

Furthermore, hereinafter the terms "preferably", "in particular", "by way of example" or similar terms are used in conjunction with optional features, without alternative embodiments thereby being restricted. In this regard, features introduced by these terms are optional features, and there is no intention to restrict the scope of protection of the claims, and in particular of the independent claims, by these features. In this regard, the invention, as will be recognized by the person skilled in the art, can also be carried out using other configurations. Similarly, features introduced by "in one embodiment of the invention" or "in one exemplary embodiment of the invention" are to be understood to be optional features, without this being intended to restrict alternative refinements or the scope of protection of the independent claims. Furthermore, all possibilities of combining the features introduced by these introductory expressions with other features, whether optional or non-optional features, are intended to remain unaffected by said introductory expressions.

A CEM scanner probe includes a probe shaft, a probe tip arranged at a distal end of the probe shaft, a probe body, and a probe umbilical. The CEM scanner probe is provided with a sterile sheath for enclosing the CEM scanner probe. The sterile sheath includes a sheath tube configured to receive the probe shaft and has a distal tube end, a proximal tube end, a sheath tip mounted at the distal tube end of the sheath tube, and a sheath socket configured to receive the probe body. The sheath socket has a distal socket end and a proximal socket end. The proximal tube end of the sheath tube, which points away from the patient, is affixed to the sheath socket at the distal socket end of the sheath socket. The sterile sheath further includes a sheath lock ring and a sheath drape mounted with the sheath lock ring on the sheath socket at the proximal socket end which points towards the scanner cable and the confocal imaging main system.

According to an aspect of the invention, the sheath tip includes a circular optical window with an outer circular surface and an inner circular surface, and a tip shaft on which the distal tube end of the sheath tube is affixed, the sheath tip has a cylindrical shape which defines a cylinder axis and the cylinder axis defines an optical axis of the sheath tip, and the outer circular surface and the inner circular surface of the circular optical window are arranged in parallel and orthogonal to the optical axis of the sheath tip.

The probe body has a first polygonal cross section, and the sheath socket has a second polygonal cross section which substantially matches the first polygonal cross section of the probe body to permit a clamp-on navigation marker tool adapter of a surgical navigation system to be securely mounted on the sheath socket. In this context, substantially means that the sheath socket is made of a thin material and "repeats" or "copies" the polygonal cross section of the probe body 103 onto its outside to permit a clamp-on navigation marker tool adapter designed for the probe body of the CEM scanner probe to be mounted on the sheath socket.

According to another aspect of the invention, the sheath tip including the circular optical window is entirely molded from a transparent plastic material.

According to yet another aspect of the invention, the circular optical window is made of glass overmolded by a transparent plastic material.

The sheath tip includes a tip shoulder surrounding the circular optical window. The probe tip rests on the tip shoulder when the CEM scanner probe is enclosed by the sterile sheath thereby defining a predetermined distance between the circular optical window and the probe tip, i.e., a position of the circular window relative to the probe tip. The tip shoulder ensures that the axes of the sheath tip and of the probe tip are in line.

The distal tube end of the sheath tube is affixed to the tip shaft by at least one of gluing or welding.

The tip shaft has a rounded edge facing away from the circular optical window to permit an unobstructed sliding of the probe tip into the sheath tip when the sterile sheath is pulled over the CEM scanner probe.

According to another aspect of the invention, the probe body has an outer body diameter, the sheath socket is made of an elastic material, and has a central axis and an inner socket diameter. The inner socket diameter is smaller than the outer body diameter in a state in which the sheath socket is not pulled over the probe body. The probe body and the sheath socket conjointly define a fastening arrangement which permits the sheath socket to be widened in a direction transverse to the central axis as the sheath socket is pulled over the probe body when the sterile sheath is pulled over the CEM scanner probe to thereby securely affix the sterile sheath to the CEM scanner probe by a friction between the sheath socket and the probe body.

According to a further aspect of the invention, the probe shaft is an ergonomically bend probe shaft. The sheath tube is made of an elastic material to permit the sterile sheath to be pulled over the ergonomically bend probe shaft. The distal socket end of the sheath socket has a conical shape. The sheath tube is widened in a direction transverse to the central axis at the proximal tube end to fit on the distal socket end having the conical shape, and the sheath tube is affixed to the tip sheath socket at the distal socket end by at least one of gluing or welding.

According to yet a further aspect of the invention, the sterile sheath further includes a sheath adaptor arranged between the proximal tube end of the sheath tube and the distal socket end of the sheath socket, the sheath adaptor being made of an elastic material to permit the sterile sheath to be pulled over the ergonomically bend probe shaft.

The probe body defines a circumferential groove provided on an outer surface at a distal end of the probe body. The sheath socket may include a clamp-on element provided on an inner surface of the sheath socket and corresponding to the circumferential groove. The circumferential groove and the clamp-on element conjointly define a fastening arrangement to securely affix the sheath socket on the probe body by clamping the clamp-on element on the circumferential groove when the sterile sheath is pulled over the CEM scanner probe. "Clamping" in the context of this invention means securely snapping-on, engaging, snapping into place, or locking into place.

The clamp-on element may be formed by at least one of ridges, a textured surface, or a plurality of sheath socket tongues protruding from the inner surface of the sheath socket. The clamp-on element may also be formed by pins inserted tangentially in the sheath socket.

According to another aspect of the invention, the probe body is made of magnetic material or includes inserts made of the magnetic material. The sheath socket includes at least one sheath socket locking magnet. The magnetic material and the at least one sheath socket locking magnet define a fastening arrangement to securely affix the sheath socket on the probe body by magnetically fixating the sheath socket on the probe body when the sterile sheath is pulled over the CEM scanner probe.

According to a further aspect of the invention, the probe body includes at least one probe body pin protruding from an outer surface of the probe body and the sheath socket includes at least one sheath socket female bayonet contour provided on an inner surface of the sheath socket. According to this aspect of the invention, the at least one probe body pin moves inside the at least one sheath socket female bayonet contour as the sheath socket is rotated relative to the probe body in a fastening direction to securely affix the sheath socket on the probe body when the sterile sheath is pulled over the CEM scanner probe.

According to yet another aspect of the invention, the sheath socket includes at least one sheath socket pin protruding from an inner surface of the sheath socket and the probe body includes at least one probe body female bayonet contour provided on the outer surface of the probe body. According to this aspect of the invention, the at least one sheath socket pin moves inside the at least one probe body female bayonet contour as the sheath socket is rotated relative to the probe body in a fastening direction to securely affix the sheath socket on the probe body when the sterile sheath is pulled over the CEM scanner probe.

The object is further achieved by providing a method for securely affixing a sterile sheath to a CEM scanner probe, the CEM scanner probe including a probe body, a probe shaft, and a probe tip, and the sterile sheath including a sheath socket configured to receive the probe body. The method includes: conjointly defining a fastening arrangement by the probe body and the sheath socket, pulling the sterile sheath over the CEM scanner probe, and securely affixing the sheath socket on the probe body with the fastening arrangement.

According to an aspect of the invention, the fastening arrangement includes a circumferential groove provided on an outer surface at a distal end of the probe body and a clamp-on element corresponding to the circumferential groove of the probe body and provided on an inner surface of the sheath socket, and the sheath socket is securely affixed on the probe body by clamping the clamp-on element on the circumferential groove. According to this aspect of the invention, the clamp-on element is formed by at least one of ridges, a textured surface, a plurality of sheath socket tongues protruding from the inner surface of the sheath socket, or pins inserted tangentially in the sheath socket.

According to another aspect of the invention, the fastening arrangement is conjointly defined by the sheath socket being made of an elastic material and by providing the sheath socket with an inner socket diameter being smaller than an outer body diameter of the probe body in a state in which the sheath socket is not pulled over the probe body. According to this aspect of the invention, the sterile sheath is securely affixed to the CEM scanner probe by widening the sheath socket in a direction transverse to a central axis of the sheath socket when the sheath socket is pulled over the probe body, thereby creating friction between the sheath socket and the probe body.

According to yet another aspect of the invention, the method further includes: providing the sheath tube with a first longitudinal length being shorter than a second longitudinal length defined by the probe shaft and the probe tip, and the sheath tube being made of the elastic material, pulling the sheath tube over the probe tip and the probe shaft, thereby widening the sheath tube in a longitudinal direction, surrounding the circular optical window by a tip shoulder, thereby defining a predetermined distance between the circular optical window and the probe tip to permit the probe tip to rest on the tip shoulder; and pressing the probe tip against the sheath tip by a tension generated by the sheath tube widened in the longitudinal direction.

BRIEF DESCRIPTION OF THE DRAWINGS

The invention will now be described with reference to the drawings wherein:

FIG. 6C shows an enlarged portion of the sectional view of the probe body in FIG. 6B.

DESCRIPTION OF EXEMPLARY EMBODIMENTS

Figure 1:
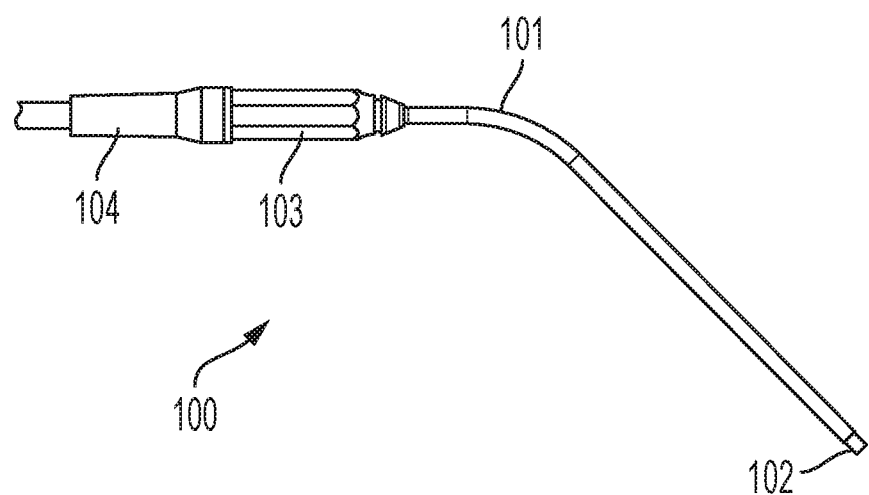
FIG. 1 shows a schematic illustration of a CEM scanner probe.

In the following description, the same reference numerals are used for the same elements when they are depicted in different drawings. The features defined in the description, such as detailed construction and elements, are provided to assist in a comprehensive understanding of the invention. Thus, it is apparent that various embodiments of the present invention can be carried out without those specifically defined features. Also, functions or elements known in the related art are not described in detail since they would obscure the invention with unnecessary detail.

FIG. 1 is a schematic illustration of a CEM scanner probe 100 for confocal laser scanning imaging that enables real-time visualization. The CEM scanner probe 100 is an optical surgical instrument which can be used as a digital biopsy tool that helps to support the resection of brain tumors. With the help of the CEM scanner probe 100, neurosurgeons are able to perform a digital biopsy without the need for tissue extraction.

The CEM scanner probe 100 in FIG. 1 includes a probe shaft 101, a probe tip 102, a probe body 103, and a probe umbilical 104. The probe shaft 101 typically has a relatively small diameter of 4 mm. The probe tip 102 includes a probe tip window 105 (shown in FIG. 5) through which an illuminating confocal laser beam is emitted and the returning light is collected. The probe tip window 105 has a thickness of from 300 µm to <400 µm to permit optimal confocal imaging. The probe tip window 105 is typically made of glass or of plastic material with optical properties similar to glass. The panes of the probe tip window 105 are provided precisely parallel to one another and orthogonal to the optical axis of the probe tip 102 for optimal confocal imaging.

The probe shaft 101 has either a straight or an ergonomically bend shape. The probe body 103 is provided to hold the scanner. The probe body 103 has a polygonal cross section, e.g., an octagonal cross section, to permit secure adaptation of one or more beacons or navigation markers 1140 shown in FIG. 11 for a surgical navigation system (IGS—Image Guided Surgery System).

A cable or umbilical 104 provides electrical and optical connection to a main system (not shown) including laser, photo detector, microelectronics for control and image handling, trolley, and housing.

Since the CEM scanner probes for confocal laser scanning imaging, such as the CEM scanner probe 100 shown in FIG. 1, have sensitive components and are too delicate to be sterilized, a sterile sheath 200 is provided to enclose the non-sterile CEM scanner probe 100 shown in FIG. 1.

Figure 2:
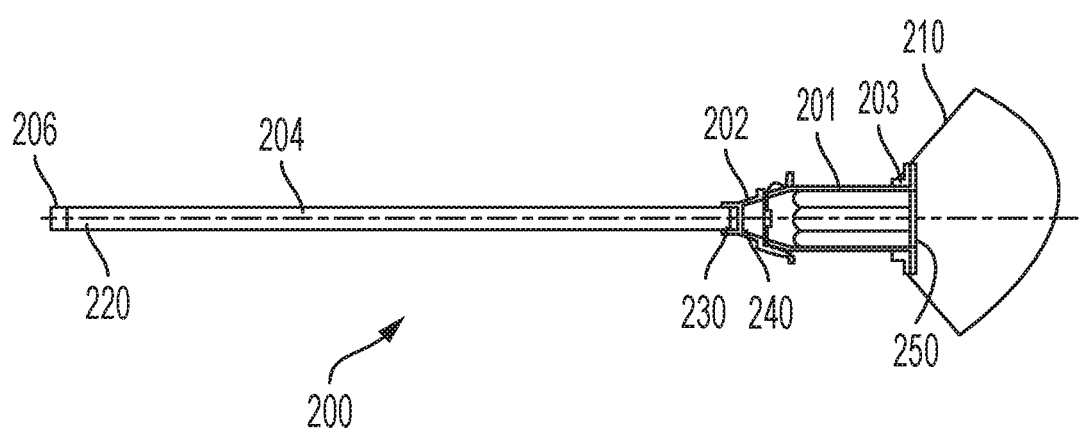
FIG. 2 shows a sterile sheath for enclosing the CEM scanner probe shown in FIG. 1 according to an exemplary embodiment of the invention.

The sterile sheath 200 according to an exemplary embodiment of the invention is shown in FIG. 2. The sterile sheath 200 includes a sheath socket 201, a sheath adaptor 202, a sheath lock ring 203, a sheath tube 204, a sheath tip 206, and a sheath drape 210. The sheath tube 204 has a distal tube end 220 and a proximal tube end 230. Likewise, the sheath socket 201 has a distal socket end 240 and a proximal socket end 250.

The sheath tube 204 is configured to receive the probe shaft 101 and has a thickness that does not significantly increase the diameter of the shaft when the sheath tube 204 encloses the probe shaft 101.

The sheath tip 206 is mounted at the distal tube end 220 of the sheath tube 204. The sheath tube 204 can be glued or welded to the sheath tip 206. In addition, a two-component molding process can be employed to affix the sheath tube 204 to the sheath tip 206. The sheath tube 204 provides a flexible sterile barrier, tight seals with the sheath tip 206 and the sheath socket 201, and elasticity.

Figure 7:
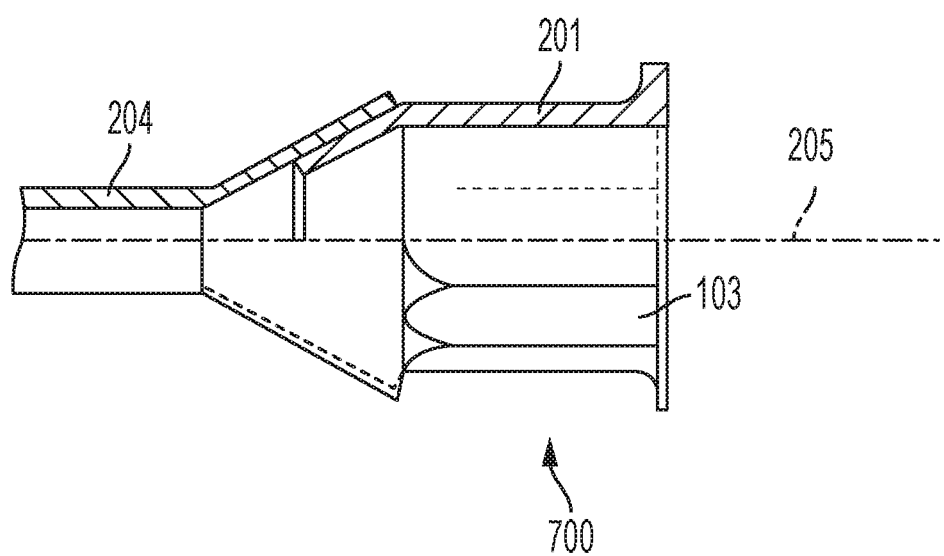
FIG. 7 shows a first fastening arrangement of a sheath socket affixed to the probe body by friction.
Figure 8:
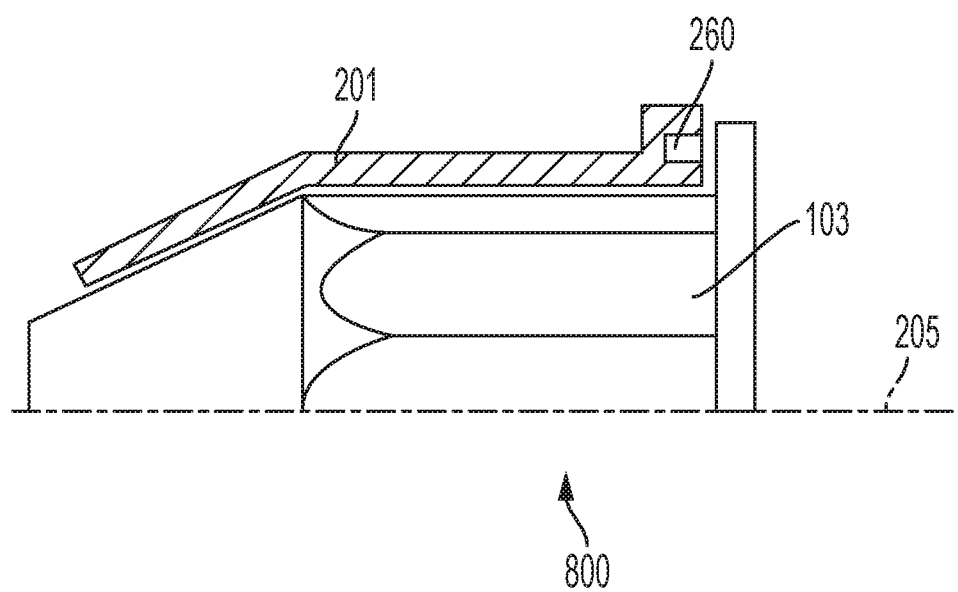
FIG. 8 shows a second fastening arrangement of a sheath socket affixed to the probe body by a magnet.
Figure 9:
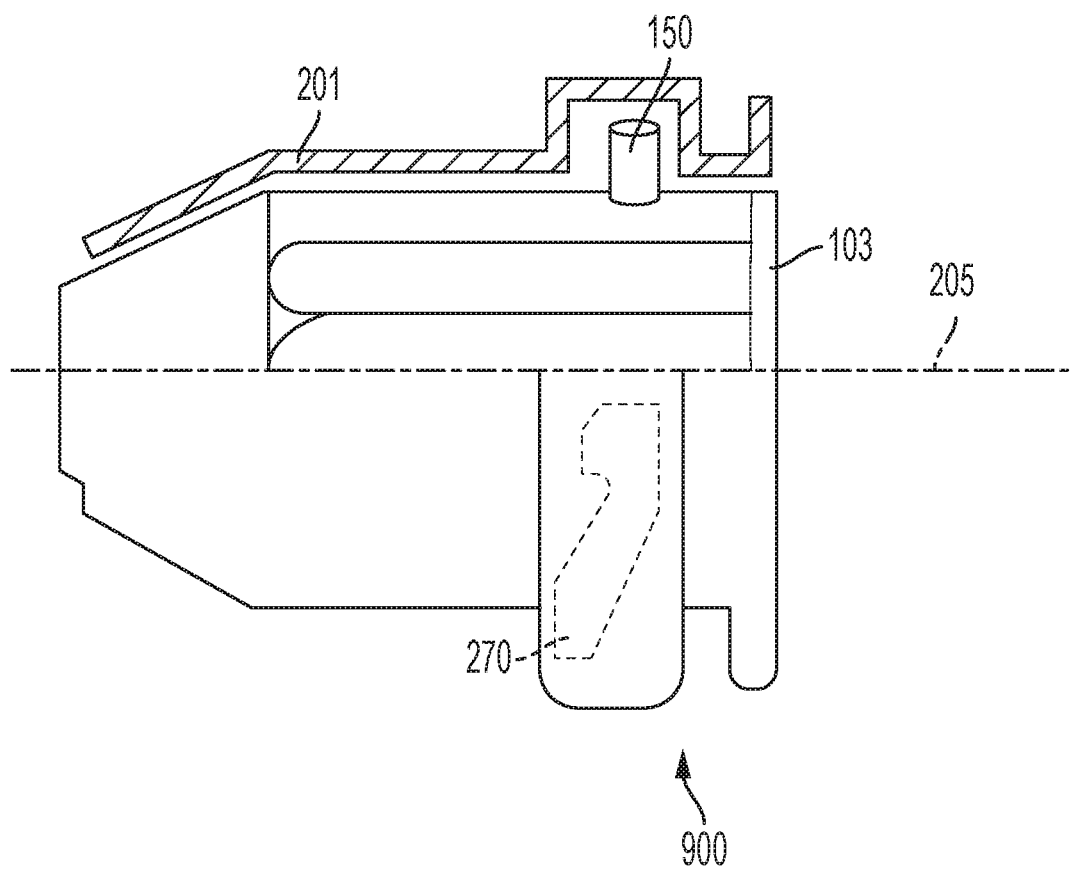
FIG. 9 shows a third fastening arrangement of a sheath socket affixed to the probe body by a bayonet-like locking mechanism.

The sheath socket 201 has a central axis 205 (shown, e.g., in FIGS. 7 to 9) and is pulled over the probe body 103 when the CEM scanner probe 100 is enclosed by the sterile sheath 200. The sheath socket 201 may be made of an elastic material and may be affixed to the probe body 103 by friction between the sheath socket 201 and the probe body 103 (as shown in FIG. 7), thereby securely affixing the entire sterile sheath 200 to the CEM scanner probe 100. The sheath socket 201 may also be affixed to the probe body 103 by fastening arrangements 800 and 900, as shown in FIGS. 8 and 9, thereby securely affixing the entire sterile sheath 200 to the CEM scanner probe 100.

The sheath socket 201 is configured to permit haptic and acoustically noticeable feedback for indicating a secure connection. The sheath socket 201 "repeats" or "copies" the polygonal cross section of the probe body 103 onto its outside, or is sufficiently flexible to allow secure adaptation of the navigation beacon(s) for the IGS via a clamp-on navigation marker tool adapter 1100 shown in FIG. 11.

The sheath socket 201 is made of a transparent material that allows observation of a laser-on LED 140 provided on the probe body 103. In addition, the sheath socket 201 provides a secure grip to the user while holding the CEM scanner probe when imaging.

The sheath adaptor 202 shown in FIG. 2 is arranged between the proximal tube end 230 of the sheath tube 204 and the distal socket end 240 (the end pointing towards the patient) of the sheath socket 201. The sheath adaptor 202 is made of an elastic material to permit the sterile sheath 200 to be pulled over an ergonomically bend probe shaft 101. If a sheath adaptor 202 is utilized, the sheath tube 204 is typically very thin and does not need to be widened.

If the sheath tube 204 is made of elastic material and the proximal tube end 230 and the opening of the sheath socket 201 at its distal socket end 240 are widened, the sheath adaptor 202 can be omitted. If both, the sheath socket 201 and the sheath tube 204 are made of elastic material, the sheath socket 201 and sheath tube 204 can be made as one piece.

The sheath drape 210 provides a sterile barrier or cover for the cable 104 connecting the probe body 103 with the imaging system (not shown). The sheath drape 210 is made of a flexible material that allows telescopic folding for room-saving packing, for example in a sterile pouch, and for easy extending when affixing the sterile sheath 200 to the CEM scanner probe 100.

Figure 3A:
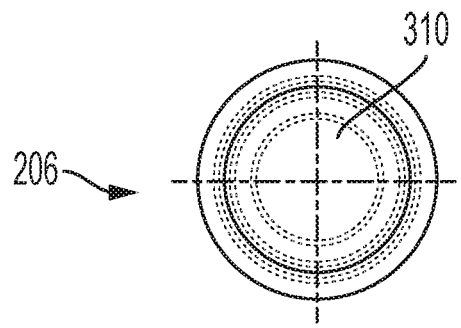
FIG. 3A shows a front view of a sheath tip according to an exemplary embodiment of the invention.
Figure 3B:
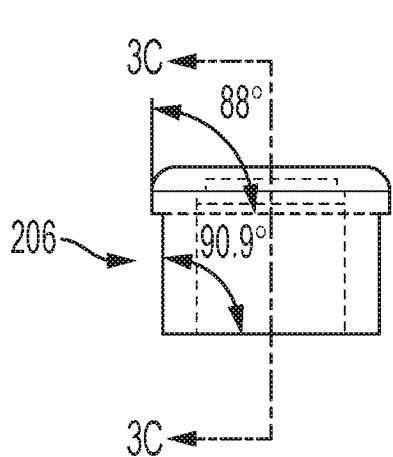
FIG. 3B shows a side view of the sheath tip shown in FIG. 3A.
Figure 3C:
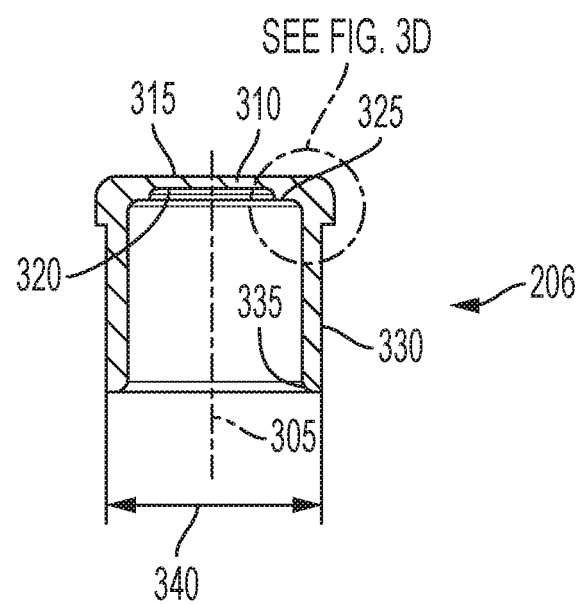
FIG. 3C shows a sectional view of the sheath tip shown in FIG. 3B.

FIGS. 3A, 3B, and 3C show front, side and sectional views, respectively, of sheath tip 206. As shown in FIGS. 3A to 3C, sheath tip 206 includes in its center a circular optical window 310. The circular optical window 310 is molded from transparent plastic material and has a diameter of 2.7 mm. As shown in FIG. 3C, circular optical window 310 has an outer surface 315 and an inner surface 320 which define a thickness of the circular optical window 310 of at least 300 µm but not more than 400 µm. The outer surface 315 and the inner surface 320 of the circular optical window 310 are machined with a very high precision and are arranged parallel to each other and orthogonal to the optical axis 305.

Figure 3D:
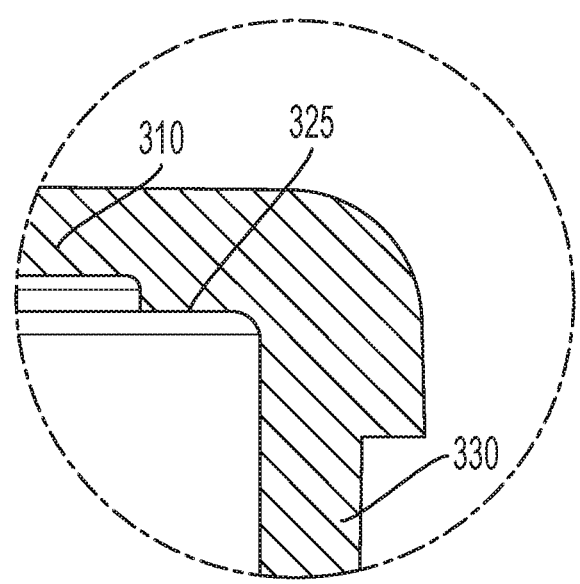
FIG. 3D is an enlarged portion of the sectional view of the sheath tip in FIG. 3C.

As illustrated in FIGS. 3C and 3D, the sheath tip 206 further includes a tip shoulder 325 surrounding the circular optical window 310 and permitting the probe tip 102 to rest on the tip shoulder 325 when the probe tip 102 is pressed against the sheath tip 206 by a tension generated by the sheath tube 204 widened in a longitudinal direction, for example. In other words, the sheath tube 204 may be shorter than the corresponding length of the probe shaft 101 and the probe tip 102.

By being made of an elastic material, this causes the sheath tip 206, 406 to be pulled securely against the probe tip 102. By appropriate dimensioning the diameters of inner diameter of the sheath tip 206, 406 and the outer diameter of the probe tip 102, as well as of the tip shoulder 325, it can be ensured that the sheath tip 206 during application of the CEM scanner probe 100 is correctly positioned on the probe tip 102.

In particular, the tip shoulder 325 ensures a predetermined distance of 0.5 mm+/−0.005 mm between the circular optical window 310 (or the circular optical window 410 made of glass shown in FIG. 4) and the probe tip window 105.

The tip shoulder 325 may be formed as a ring, as shown in FIGS. 3A to 3D, but is not limited thereto. Instead, the tip shoulder may also be formed by a plurality of protrusions (not shown), for example.

Sheath tip 206 further includes tip shaft 330 and a rounded edge 335. The tip shaft 330 permits the sheath tube 204 to be affixed at its distal tube end 220 to the sheath tip 206, e.g., by gluing or welding. The rounded edge 335 has a radius of 0.2 mm, faces away from the circular optical window 310, and allows easy sliding of the probe tip 102 into the sheath tip 206 to prevent catching of the sheath tip at the tip shaft 330 during insertion. In other words, the rounded edge 335 is configured to permit a smooth or unobstructed sliding of the probe tip 102 into the sheath tip 206 when the sterile sheath 200 is pulled over the CEM scanner probe 100. In other words, the rounded edge 335 prevents the probe tip 102 from getting caught at the tip shaft 330 when the probe tip 102 is inserted into the sheath tip 206.

Figure 4:
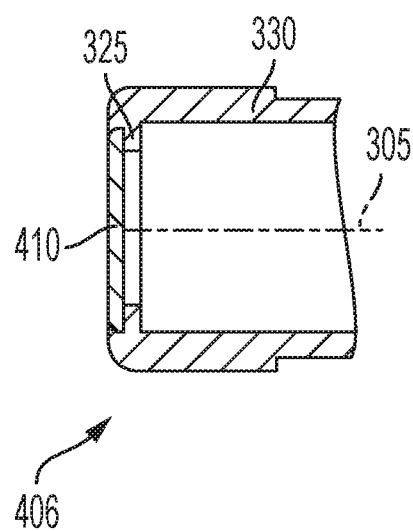
FIG. 4 shows a sectional view of a sheath tip according to another exemplary embodiment.

FIG. 4 shows a sectional view of a sheath tip 406 which is provided with a circular optical window 410 made of glass. As shown in FIG. 4, the circular optical window 410 is overmolded on its outer edges to provide a secure fixation to the sheath tip 406. Similar to the sheath tip 206 shown in FIGS. 3A to 3D, sheath tip 406 includes tip shoulder 325 and tip shaft 330.

Figure 5:
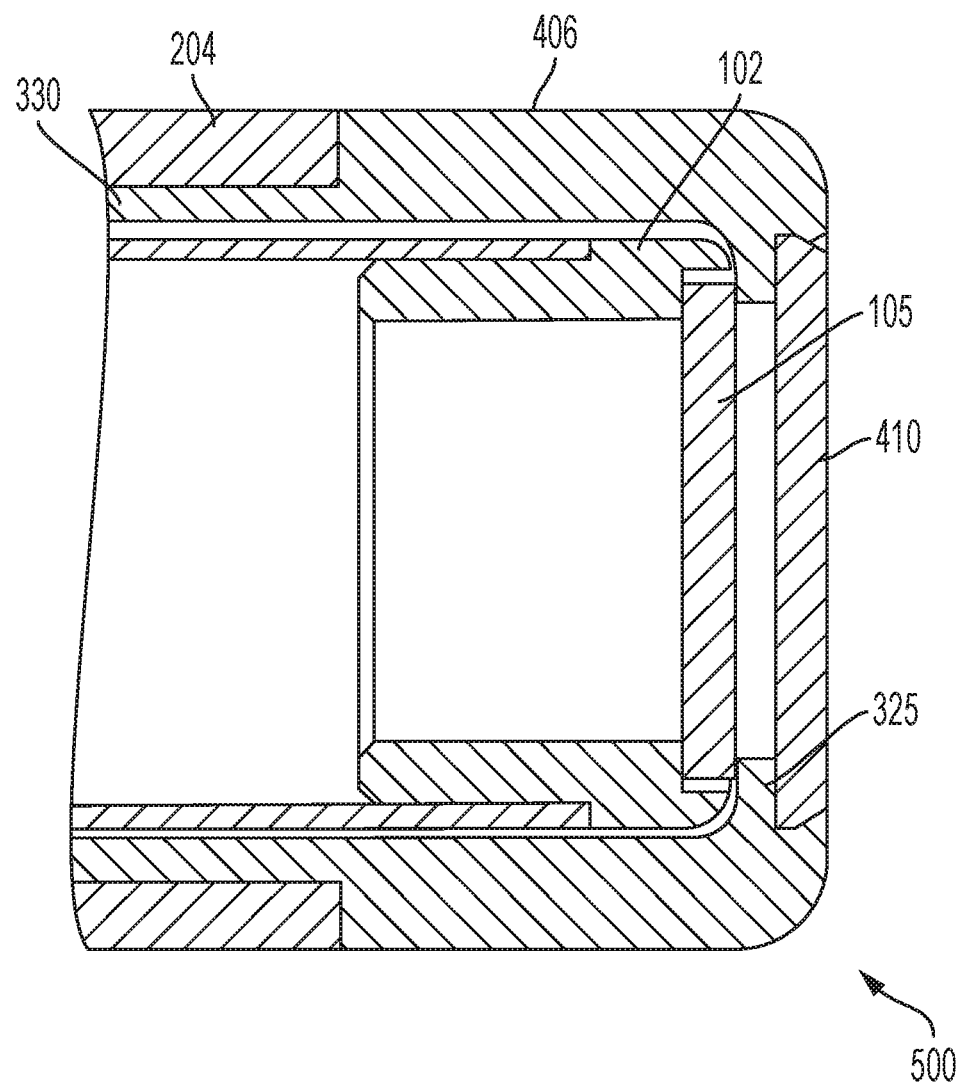
FIG. 5 shows a sectional view of a sheath tip arrangement in which a probe tip of the CEM scanner probe is enclosed by the sheath tip.

FIG. 5 shows a sectional view of a sheath tip arrangement 500 in which a probe tip 102 of the CEM scanner probe 100 is enclosed by the sheath tip 406, and the sheath tip 406 is pulled securely against the probe tip 102. As also shown in FIG. 5, sheath tube 204 is attached to tip shaft 330 so that a smooth continuous outer surface of the sheath tip 406 is obtained. Although FIG. 5 shows an arrangement with sheath tip 406 with a circular optical window 410 made of glass, it is also possible to utilize sheath tip 206 shown in FIGS. 3A to 3D in the sheath tip arrangement 500 instead.

Figure 6A:
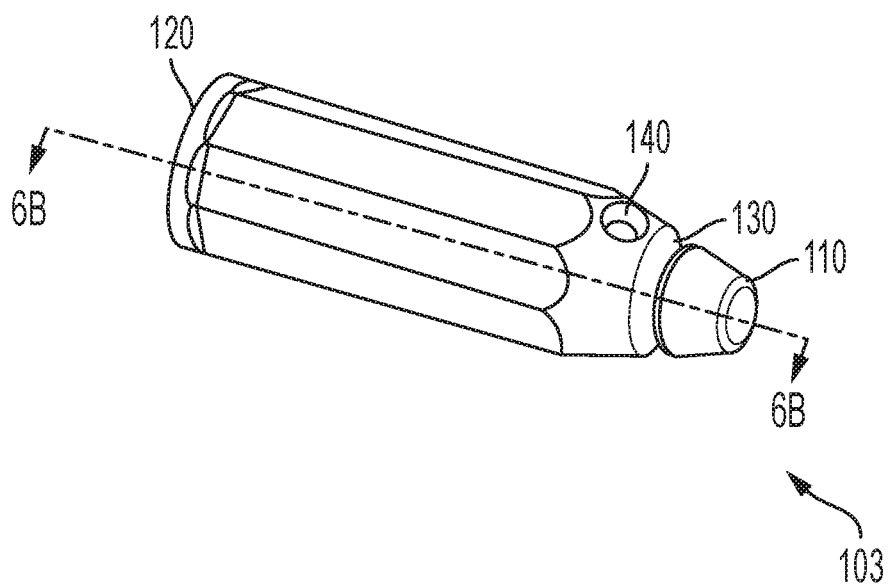
FIG. 6A shows a perspective view of a probe body.

FIG. 6A shows a perspective view of a probe body 103. As shown in FIG. 6A, probe body 103 has a distal end (pointing towards the patient) and a proximal end 120. The probe body 103 shown in FIG. 6A has an octagonal cross section which permits secure adaptation of a clamp-on navigation marker tool adapter 1100. Probe body 103 further includes light-emitting diode (LED) 140 for indicating "laser-on" and a circumferential groove 130.

Figure 6B:
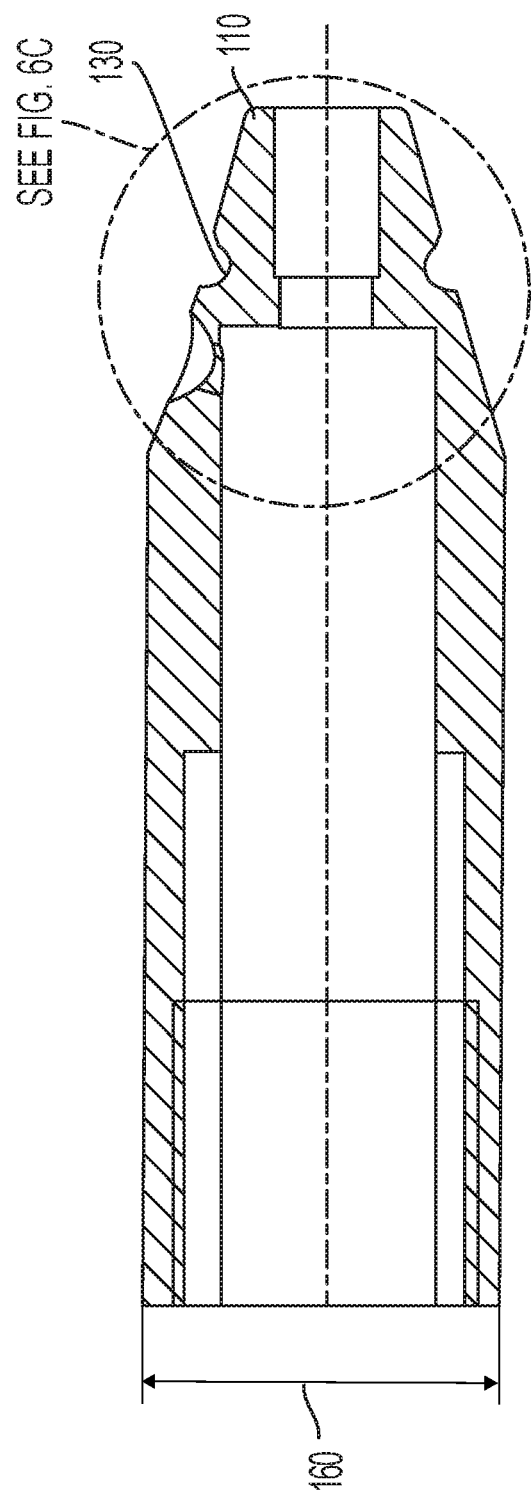
FIG. 6B shows a sectional view of the probe body shown in FIG. 6A.

FIG. 6B shows a sectional view of the probe body shown in FIG. 6A, and FIG. 6C shows an enlarged portion of the sectional view of the probe body in FIG. 6B, in which the circumferential groove 130 at the distal end 110 of the probe body 103 is depicted in more detail.

FIG. 7 shows a first fastening arrangement 700 of a sheath socket 201 affixed to the probe body 103. As shown in FIG. 7, the distal socket end 240 of the sheath socket 201 has a conical shape and a widened opening. The sheath tube 204 is also widened in a direction transverse to the central axis 205 at the proximal tube end 230 to fit on the distal socket end 240 having the conical shape and a widened opening. If the opening of the sheath socket 201 is sufficiently wide and the sheath tube 204 is made of elastic material, the sheath adaptor 202 can be omitted, as shown in FIG. 7. That is, the elasticity of the sheath tube 204 and the widened opening of the sheath socket 201 allow the sterile sheath 200 to be easily pulled over an ergonomically bend probe shaft 101. If both, the sheath socket 201 and the sheath tube 204 are made of elastic material, the sheath socket 201 and sheath tube 204 can be made as one piece.

As shown in FIG. 7, the sheath tube 204 is affixed to the sheath socket 201 at the distal socket end 240 by at least one of gluing or welding. As shown in FIG. 6B, the probe body 103 has an outer body diameter 160. The sheath socket 201 can be made of an elastic material. The sheath socket 201 has a central axis 205 and an inner socket diameter 290 (as shown, e.g., in FIG. 10C), and the inner socket diameter 290 can be made smaller than the outer body diameter 160 in a state in which the sheath socket 201 is not pulled over the probe body 103. In this exemplary embodiment, the elastic material of the sheath socket 201 permits the sheath socket 201 to be widened in a direction transverse to the central axis 205 as the sheath socket 201 is pulled over the probe body 103 when the sterile sheath 200 is pulled over the CEM scanner probe 100 to thereby securely affix the sterile sheath 200 to the CEM scanner probe 100 by a friction between the sheath socket 201 and the probe body 103.

FIG. 8 shows a second fastening arrangement 800 of a sheath socket 201 affixed to the probe body by one or more sheath socket locking magnets 260. In this exemplary embodiment, the probe body 103 is made of a magnetic material or has inserts made from a magnetic material. The sheath socket 201 includes one or more sheath socket locking magnets 260. In the assembled state, the magnets lock onto the magnetic material of the probe body 103 and ensure a secure seating of the sheath socket 201 on the probe body 103.

It is also possible to provide the magnets in or at the probe body 103, and the sheath socket 201 carries one or more elements made of magnetic material.

FIG. 9 shows a third fastening arrangement 900 of a sheath socket 201 affixed to the probe body 103 by a screw or bayonet-like locking mechanism. According to this exemplary embodiment of the invention, the probe body 103 includes one or more probe body pins 150 protruding from an outer surface of the probe body 103 and the sheath socket 201 includes corresponding one or more female bayonet contours 270 for a bayonet-like locking mechanism. Which of the two mating parts, i.e., sheath socket 201 or probe body 103, carries the female bayonet contours 270 and which of the mating parts carries the pin part is exchangeable.

The mechanism may be formed in a way that it can only be securely locked one time, preventing reuse of the single use sterile sheath 200.

Referring back to FIG. 6A which shows circumferential groove 130 of the probe body 103 provided on an outer surface at a distal end 110 of the probe body 103. The sheath socket 201 may include a clamp-on or "snap on" element provided on an inner surface of the sheath socket 201 and corresponding to the circumferential groove 130. The circumferential groove 130 and the clamp-on element conjointly define a fastening arrangement to securely affix the sheath socket 201 on the probe body 103 by clamping the clamp-on element on the circumferential groove 130 when the sterile sheath 200 is pulled over the CEM scanner probe 100.

Figure 10A:
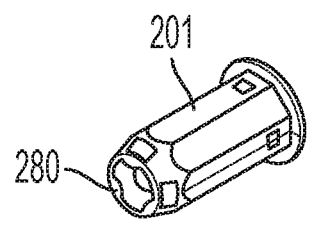
FIG. 10A shows a perspective view of a sheath socket including sheath socket tongues.
Figure 10B:
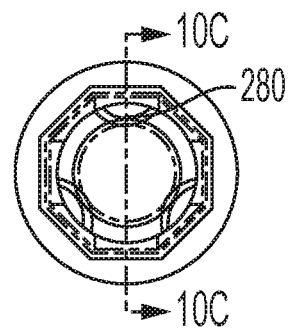
FIG. 10B shows a top view of the sheath socket shown in FIG. 10A, FIG. 10 C shows a front view of the sheath socket shown in FIG. 10A.
Figure 10C:
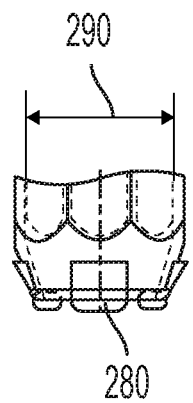

According to an exemplary embodiment of the invention, the clamp-on element is formed by sheath socket tongues 280. A perspective view of a sheath socket including sheath socket tongues 280 is shown in FIG. 10A. FIG. 10B shows a top view of the sheath socket 201 with sheath socket tongues 280 shown in FIG. 10A, and FIG. 10 C shows a front view of the sheath socket shown in FIG. 10A.

In addition, the clamp-on element may be formed by ridges and textured surfaces (not shown) protruding from the inner surface of the sheath socket 201. The clamp-on element may also be formed by pins inserted tangentially in the sheath socket 201.

Figure 11:
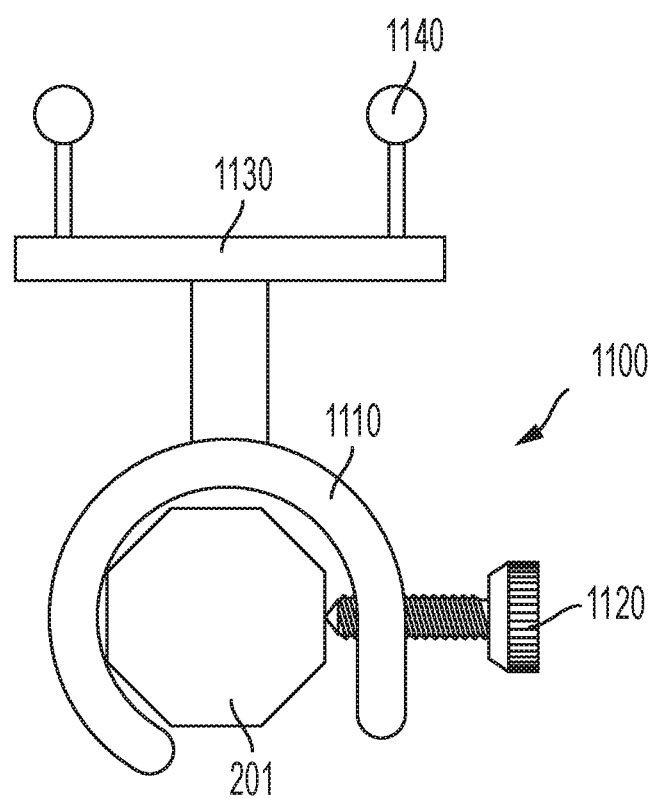
FIG. 11 shows a clamp-on navigation marker tool adapter securely mounted on the sheath socket.

FIG. 11 schematically shows a clamp-on navigation marker tool adapter 1100 securely mounted on the sheath socket 201 which is affixed to the probe body 103. The clamp-on navigation marker tool adapter 1100 includes a fastener 1110 surrounding the sheath socket 201 at least partially and a fastener screw 1120 to securely fasten the clamp-on navigation marker tool adapter 1100 on the sheath socket 201. FIG. 11 further shows navigation system holder 1130 holding two navigation markers 1140. However, any other number of navigation markers 1140 and any other design of the clamp-on navigation marker tool adapter 1100 is possible, as long as it permits the clamp-on navigation marker tool adapter 1100 to be securely fastened on the sheath socket 201 having the polygonal cross section described above.

Figure 12:
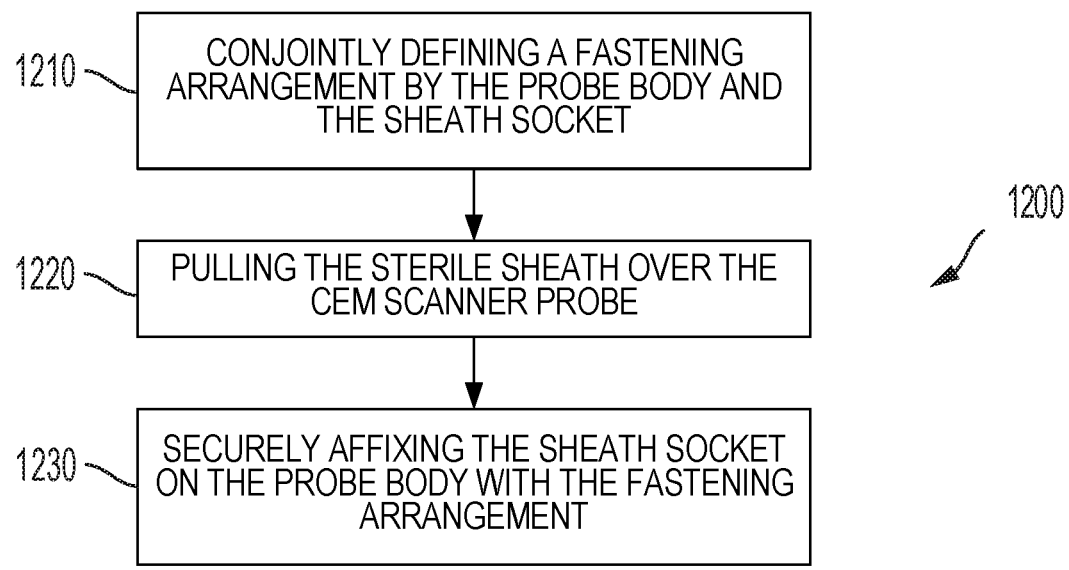
FIG. 12 shows a flow chart of a method for securely affixing a sterile sheath to a CEM scanner probe.

FIG. 12 shows a flow chart of a method 1200 for securely affixing a sterile sheath 200 to a CEM scanner probe 100. In this exemplary embodiment, the CEM scanner probe 100 includes a probe body 103, a probe shaft 101, and a probe tip 102, and the sterile sheath 200 includes a sheath socket 201 configured to receive the probe body 103.

The method begins at step 1210, at which the probe body and the sheath socket conjointly define a fastening arrangement. At step 1220, the sterile sheath 200 is pulled over the CEM scanner probe 100. The method 1200 concludes with step 1230, at which the sheath socket is securely affixed on the probe body with the fastening arrangement.

Figure 13:
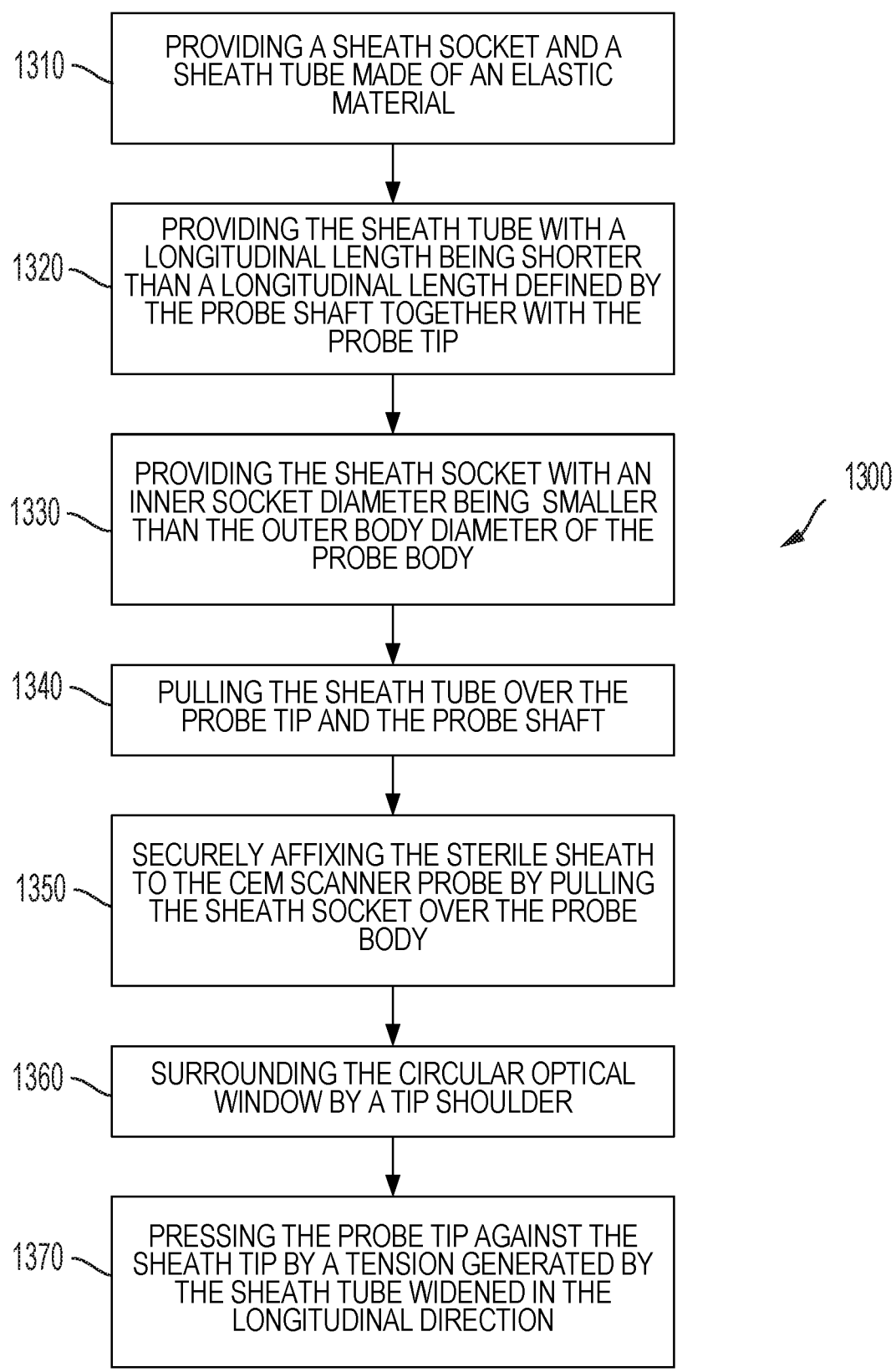
FIG. 13 shows a flow chart of a method for securely affixing a sterile sheath to a CEM scanner probe according to an exemplary embodiment of the invention.

FIG. 13 shows a flow chart of a method 1300 for securely affixing a sterile sheath 200 to a CEM scanner probe 100. In this exemplary embodiment, the CEM scanner probe 100 includes a probe shaft 101 and a probe tip 102. The probe shaft 101 together with the probe tip 102 defines a first longitudinal length. The CEM scanner probe 100 further includes a probe body 103 having an outer body diameter 160. The sterile sheath 200 includes a sheath socket 201, a sheath tube 204 has a central axis 205, and a sheath tip 206. The sheath socket 201 and the sheath tube 204 are made of an elastic material. The sheath tip 206 includes a circular optical window 310 and is mounted at a distal tube end 220 of the sheath tube 204.

The method begins at step 1310, at which a sheath socket 201 and a sheath tube 204 are provided which are made of an elastic material. The sheath tube 204 has a central axis 205. At step 1320, the sheath tube 204 is provided with a second longitudinal length that is shorter than the first longitudinal length defined by the probe shaft 101 together with the probe tip 102. The method proceeds to step 1330, at which the sheath socket 201 is provided with an inner socket diameter 290, the inner socket diameter 290 being smaller than the outer body diameter 160 of the probe body 103 in a state in which the sheath socket 201 is not pulled over the probe body 103, i.e., in a state in which the sterile sheath 200 is not installed on the CEM scanner probe 100. At step 1340, the sheath tube 204 is pulled over both the probe tip 102 and the probe shaft 101, and thereby the sheath tube 204 is widened in a longitudinal direction. By widening the sheath tube 204 in the longitudinal direction, a tension created by the sheath tube 204 which acts like a spring. At step 1350, the sterile sheath 200 is securely affixed to the CEM scanner probe 100 by pulling the sheath socket 201 over the probe body 103. Thereby, the sheath socket 201 is widened in a direction transverse to the central axis 205, and a friction between the sheath socket 201 and the probe body 103 is created that affixes the sterile sheath 200 to the CEM scanner probe 100. The method continues to step 1360 at which the circular optical window 310 is surrounded by a tip shoulder 325. This defines a predetermined distance between the circular optical window 310 and the probe tip 102 to permit the probe tip 102 to rest on the tip shoulder 325. As a result, the circular optical window 310 is precisely positioned relative to the probe tip window 105. The method ends at step 1370, at which the probe tip 102 is pressed against the sheath tip 206 by the tension generated by the sheath tube 204 widened in the longitudinal direction which holds the circular optical window 310 and the probe tip window 105 in position relative to one another. This also ensures that any adverse effects on signals passing through the probe tip window 105 and the circular optical window 310 of the sterile sheath are minimized.

Figure 14:
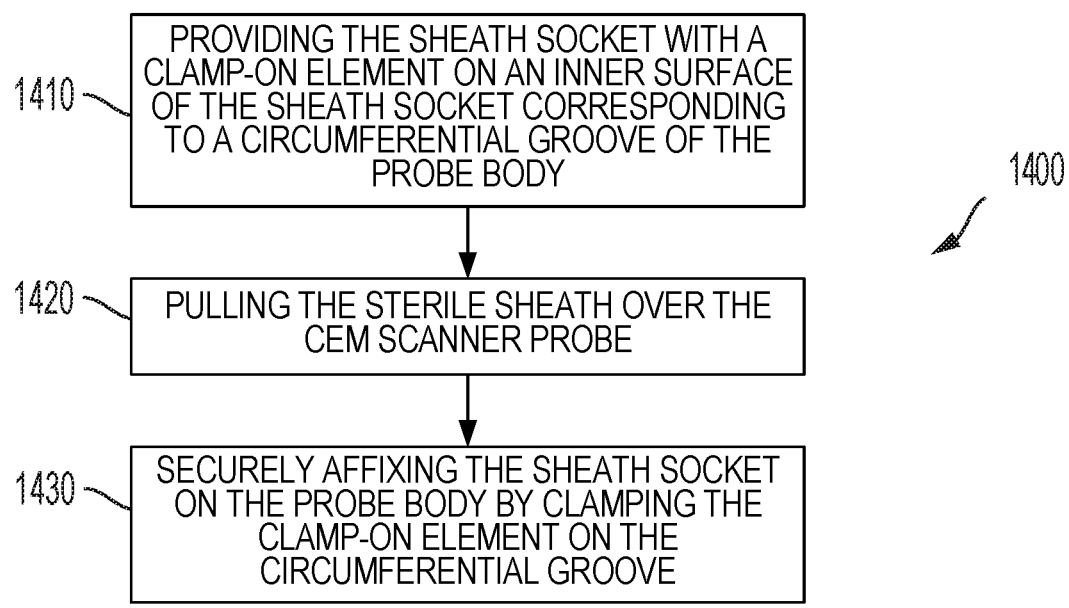
FIG. 14 shows a flow chart of a method for securely affixing a sterile sheath to a CEM scanner probe according to another exemplary embodiment of the invention.

FIG. 14 shows a flow chart of yet another method 1400 for securely affixing a sterile sheath 200 to a CEM scanner probe 100. In this exemplary embodiment, the CEM scanner probe 100 includes a probe body 103 which has a circumferential groove 130 and which is provided on an outer surface at a distal end 110 of the probe body 103. The sterile sheath 200 includes a sheath socket 201 which is configured to receive the probe body 103 by having a shape that generally matches the shape of the probe body 103.

The method begins at step 1410 at which the sheath socket 201 is provided with a clamp-on element, such as sheath socket tongues 280, on an inner surface of the sheath socket 201 corresponding to a circumferential groove 130 of the probe body 103. Other clamp-on elements, such as ridges or a textured surface protruding from the inner surface of the sheath socket 201 are also possible. In addition, the clamp-on element may be formed by pins (not shown) inserted tangentially in the sheath socket 201. At 1420, the sterile sheath 200 is pulled over the CEM scanner probe 100. The method ends at step 1430, at which the sheath socket 201 is securely fixed on the probe body 103 by clamping the clamp-on element on the circumferential groove 130. In this state, similar to step 1360 in method 1200, the probe tip 102 is pressed against the sheath tip 206 by a tension which holds the circular optical window 310 and the probe tip window 105 in position relative to one another. The tension may be generated when the sheath socket 201 is securely affixed on the probe body 103 by widening the sheath tube 204 in the longitudinal direction, by providing an elastic sheath adaptor 202 between the sheath tube 204 and widening the sheath adaptor 202 in the longitudinal direction, and/or by providing the sheath socket 201 with an elasticity and widening the sheath socket 201 in the longitudinal direction.

In summary, a sterile sheath 200 for enclosing a non-sterile CEM scanner probe 100 is provided which is easy to be applied to the CEM scanner probe 100 prior to imaging and which is easy to be removed thereafter. The sterile sheath 200 is intended for single use, is robust and disposable. Thereby, costs can be reduced. In addition, various fastening arrangements allow to easily affix the sheath socket 201 to the probe body 103 and to precisely positioning of the circular optical window 310 relative to the probe tip window 105, which minimizes adverse effects on signals passing through the circular optical window 310 of the sterile sheath 200 and the probe tip window 105.

It is understood that the foregoing description is that of the exemplary embodiments of the invention and that various changes and modifications may be made thereto without departing from the spirit and scope of the invention as defined in the appended claims.

LIST OF REFERENCE NUMERALS

100 CEM scanner probe
101 Probe shaft
102 Probe tip
103 Probe body
104 Probe umbilical
105 Probe tip window
110 Distal end of probe body
120 Proximal end of probe body
130 Circumferential groove
140 Laser-on LED
150 Probe body pin
200 Sterile sheath
201 Sheath socket
202 Sheath adaptor
203 Sheath lock ring
204 Sheath tube
205 Central axis
206 Sheath tip
210 Sheath drape
220 Distal tube end
230 Proximal tube end
240 Distal socket end
250 Proximal socket end
260 Sheath socket locking magnet
270 Sheath socket female bayonet contour
280 Sheath socket tongue
290 Inner socket diameter
305 Optical axis
310 Circular optical window
315 Outer surface of the circular optical window
320 Inner surface of the circular optical window
325 Tip shoulder
330 Tip shaft
335 Rounded edge
340 Outer diameter of tip shaft
406 Sheath tip
410 Circular optical window made of glass 500 Sheath tip arrangement
700 First fastening arrangement
800 Second fastening arrangement
900 Third fastening arrangement
1100 Clamp-on navigation marker tool adapter
1110 Fastener
1120 Fastener screw
1130 Navigation system holder
1140 Navigation marker(s)

What is claimed is:

1. A sterile sheath for enclosing a confocal endomicroscopy (CEM) scanner probe, the CEM scanner probe including a probe shaft, a probe tip arranged at a distal end of the probe shaft, a probe body, and a probe umbilical, the sterile sheath comprising: a sheath tube configured to receive the probe shaft and having a distal tube end and a proximal tube end; a sheath tip mounted at the distal tube end of the sheath tube; a sheath socket configured to receive the probe body, the sheath socket having a distal socket end and a proximal socket end, and the proximal tube end of the sheath tube being fixed to the sheath socket at the distal socket end; a sheath lock ring; a sheath drape mounted on the sheath socket at the proximal socket end with the sheath lock ring; and a circular optical window with an outer planar circular surface and an inner circular surface, wherein the inner circular surface is planar along its entire inner portion, wherein the sheath tip includes a tip portion which is arranged orthogonal to the optical axis of the sheath tip, wherein the circular optical window is arranged in the tip portion, wherein the outer planar circular surface and the inner circular surface of the circular optical window are arranged in parallel, wherein the tip portion has a first thickness in an area of the circular optical window and a second thickness outside the area of the circular optical window, and wherein the first thickness is smaller than the second thickness, wherein the sheath tip including the circular optical window is entirely molded as one piece from a transparent plastic material with an indent, and wherein the indent is arranged in the tip portion and defines the circular optical window.

2. The sterile sheath of claim 1, wherein:
the sheath tip includes a tip shaft on which the distal tube end of the sheath tube is affixed, and
the sheath tip has a cylindrical shape which defines a cylinder axis and the cylinder axis defines the optical axis of the sheath tip.

3. The sterile sheath of claim 2, wherein:
the sheath tip further includes a tip shoulder surrounding the circular optical window, and
the probe tip rests on the tip shoulder when the CEM scanner probe is enclosed by the sterile sheath, thereby defining a predetermined distance between the circular optical window and the probe tip.

4. The sterile sheath of claim 2, wherein the distal tube end of the sheath tube is affixed to the tip shaft by at least one of gluing or welding.

5. The sterile sheath of claim 2, wherein the tip shaft has a rounded edge facing away from the circular optical window and configured to permit an unobstructed sliding of the probe tip into the sheath tip when the sterile sheath is pulled over the CEM scanner probe.

6. The sterile sheath of claim 2, wherein:
the probe body has an outer body diameter,
the sheath socket is made of an elastic material and has a central axis and an inner socket diameter, the inner socket diameter being smaller than the outer body diameter in a state in which the sheath socket is not pulled over the probe body, and
the probe body and the sheath socket conjointly define a fastening arrangement which permits the sheath socket to be widened in a direction transverse to the central axis as the sheath socket is pulled over the probe body when the sterile sheath is pulled over the CEM scanner probe to thereby securely affix the sterile sheath to the CEM scanner probe by friction between the sheath socket and the probe body.

7. The sterile sheath of claim 6, wherein:
the probe shaft is an ergonomically bend probe shaft,
the sheath tube is made of the elastic material to permit the sterile sheath to be pulled over the ergonomically bend probe shaft,
the distal socket end of the sheath socket has a conical shape,
the sheath tube is widened in the direction transverse to the central axis at the proximal tube end to fit on the distal socket end having the conical shape, and
the sheath tube is affixed to the sheath socket at the distal socket end by at least one of gluing or welding.

8. The sterile sheath of claim 1, wherein:
the probe body has a first polygonal cross section, and
the sheath socket has a second polygonal cross section which substantially matches the first polygonal cross section of the probe body to permit a clamp-on navigation marker tool adapter of a surgical navigation system to be securely mounted on the sheath socket.

9. The sterile sheath of claim 1, wherein:
the probe shaft is an ergonomically bend probe shaft, and
the sterile sheath further comprises a sheath adaptor arranged between the proximal tube end of the sheath tube and the distal socket end of the sheath socket, the sheath adaptor being made of an elastic material to permit the sterile sheath to be pulled over the ergonomically bend probe shaft.

10. The sterile sheath of claim 9, wherein:
the probe body defines a circumferential groove provided on an outer surface at the distal end of the probe body,
the sheath socket includes a clamp-on element provided on an inner surface of the sheath socket and corresponding to the circumferential groove, and
the circumferential groove and the clamp-on element conjointly define a fastening arrangement to securely affix the sheath socket on the probe body by clamping the clamp-on element on the circumferential groove when the sterile sheath is pulled over the CEM scanner probe.

11. The sterile sheath of claim 10, wherein the clamp-on element is formed by at least one of ridges, a textured surface, or a plurality of sheath socket tongues protruding from the inner surface of the sheath socket.

12. The sterile sheath of claim 10, wherein the clamp-on element is formed by pins inserted tangentially in the sheath socket.

13. The sterile sheath of claim 9, wherein:
the probe body is made of magnetic material or includes inserts made of the magnetic material,
the sheath socket includes at least one sheath socket locking magnet, and
the magnetic material and the at least one sheath socket locking magnet define a fastening arrangement to securely affix the sheath socket on the probe body by magnetically fixating the sheath socket on the probe body when the sterile sheath is pulled over the CEM scanner probe.

14. The sterile sheath of claim 9, wherein:
the probe body includes at least one probe body pin protruding from an outer surface of the probe body,
the sheath socket includes at least one sheath socket female bayonet contour provided on an inner surface of the sheath socket, and
the at least one probe body pin moves inside the at least one sheath socket female bayonet contour as the sheath socket is rotated relative to the probe body in a fastening direction to securely affix the sheath socket on the probe body when the sterile sheath is pulled over the CEM scanner probe.

15. The sterile sheath of claim 9, wherein:
the sheath socket includes at least one sheath socket pin protruding from an inner surface of the sheath socket,
the probe body includes at least one probe body female bayonet contour provided on an outer surface of the probe body, and
the at least one sheath socket pin moves inside the at least one probe body female bayonet contour as the sheath socket is rotated relative to the probe body in a fastening direction to securely affix the sheath socket on the probe body when the sterile sheath is pulled over the CEM scanner probe.

* * * * *